(12) United States Patent
Larsen et al.

(10) Patent No.: US 6,740,304 B2
(45) Date of Patent: May 25, 2004

(54) RECEPTOR BINDING CONJUGATES

(75) Inventors: Roy H. Larsen, Bekkestua (NO); Gjermund Henriksen, Mjondalen (NO)

(73) Assignee: Anticancer Therapeutic Inventions AS, Oslo (NO)

(*) Notice: Subject to any disclaimer, the term of this patent is extended or adjusted under 35 U.S.C. 154(b) by 0 days.

(21) Appl. No.: 09/731,301

(22) Filed: Dec. 5, 2000

(65) Prior Publication Data

US 2001/0008625 A1 Jul. 19, 2001

(30) Foreign Application Priority Data

Dec. 6, 1999 (NO) .......................................... 19995978

(51) Int. Cl.$^7$ .............................................. A61K 51/00
(52) U.S. Cl. .................... 424/1.49; 424/1.53; 424/1.69; 424/1.85
(58) Field of Search .............................. 424/1.49, 1.53, 424/1.65, 1.69, 1.81, 1.85, 1.57

(56) References Cited

U.S. PATENT DOCUMENTS

| | | | |
|---|---|---|---|
| 4,336,185 A | | 6/1982 | Niswender |
| 5,547,668 A | | 8/1996 | Kranz et al. |
| 5,698,178 A | * | 12/1997 | Goldenberg ............... 424/1.49 |
| 6,077,499 A | * | 6/2000 | Griffiths et al. ............ 424/1.49 |

FOREIGN PATENT DOCUMENTS

EP      0 282 057 A2      9/1988

OTHER PUBLICATIONS

Bruland et al., "Expression and Characteristics of a Novel Human Osteosarcoma–Associated Cell Surface Antigen," *Cancer Res.*, 48:5302–5309 (1988).
Bruland et al., "New Monoclonal Antibodies Specific For Human Sarcomas," *Int. J. Cancer*, 38:27–31 (1986).
Bruland, "Cancer Therapy With Radiolabeled Antibodies. An Overview," *Acta Oncol.*, 34:1085–1094 (1995).
Campbell et al., "Folate–binding Protein Is a Marker for Ovarian Cancer," *Cancer Res.*, 51:5329–5338 (1991).
Fraker et al., "Protein And Cell Membrane Iodinations With A Sparingly Soluble Chloroamide, 1,3,4,6–Tetrachloro–3a, 6a–Diphenylglycoluril," *Biochem. Biophys. Res. Comm.*, 80:849–857 (1978).
Larsen et al., "Inactivation of Human Osteosarcoma Cells In Vitro by $^{211}$At–TP–3 Monoclonal Antibody: Comparison with Astatine–211–Labeled Bovine Serum Albumin, Free Astatine–211 and External–Beam X Rays," *Radiat. Res.*, 139:178–184 (1994).
Larsen et al., "Preparation and Quality Control of $^{211}$At–Labelled and $^{125}$I–Labelled Monoclonal Antibodies. Biodistribution in Mice Carrying Human Osteosarcoma Xenografts," *J. Labelled Compds. Radiopharmaceuticals*, 34:773–785 (1994).
Larsen et al.,, "α–Particle Radiotherapy with $^{211}$At–Labeled Monodisperse Polymer Particles, $^{211}$At–Labeled IgG Proteins, and Free $^{211}$At in a Murine Intraperitoneal Tumor Model," *Gynecol. Oncol.*, 57:9–15 (1995).
Mathias et al., "Indium–111–DTPA–Folate as a Potential Folate–Receptor–Targeted Radiopharmaceutical," *J. Nucl. Med.*, 39:1579–1585 (1998).
Shinoda et al., "In Vivo Fate of Folate–BSA in Non–Tumor– and Tumor–Bearing Mice," *J. Pharm. Sci.*, 87:1521–1526 (1998).
Trippett et al., "Therapeutic Strategies Targeting Proteins That Regulate Folate and Reduced Folate Transport," *J. Chemotherapy*, 11:3–10 (1999).
Reddy et al., "Folate–Mediated Targeting of Therapeutic and Imaging Agents to Cancers," *Critical Reviews in Therapeutic Drug Carrier Systems*, 15:587–627 (1998).

\* cited by examiner

*Primary Examiner*—Michael G. Hartley
(74) *Attorney, Agent, or Firm*—Paul T. Clark; Clark & Elbing LLP

(57) ABSTRACT

The present invention relates to a receptor binding conjugate which consists of an antibody, a radionuclide and folate or a folate derivative, wherein or not the conjugate possesses dual binding ability. The present invention also relates to a method and a kit to prepare, as well as a method to use, such conjugates.

Figure 1:
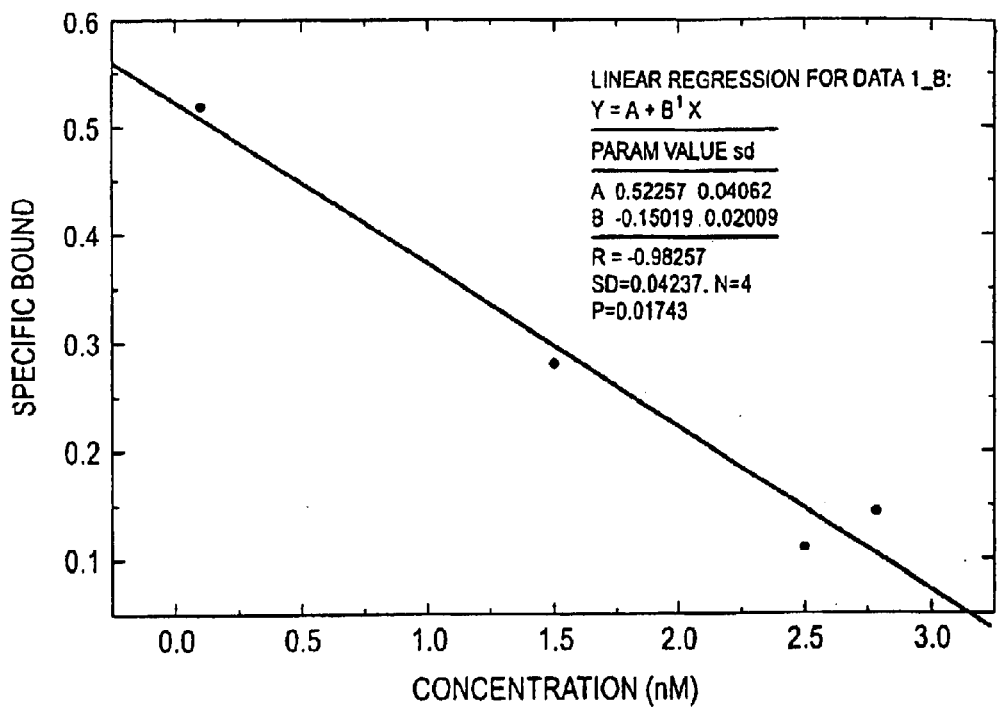
Figure 1:
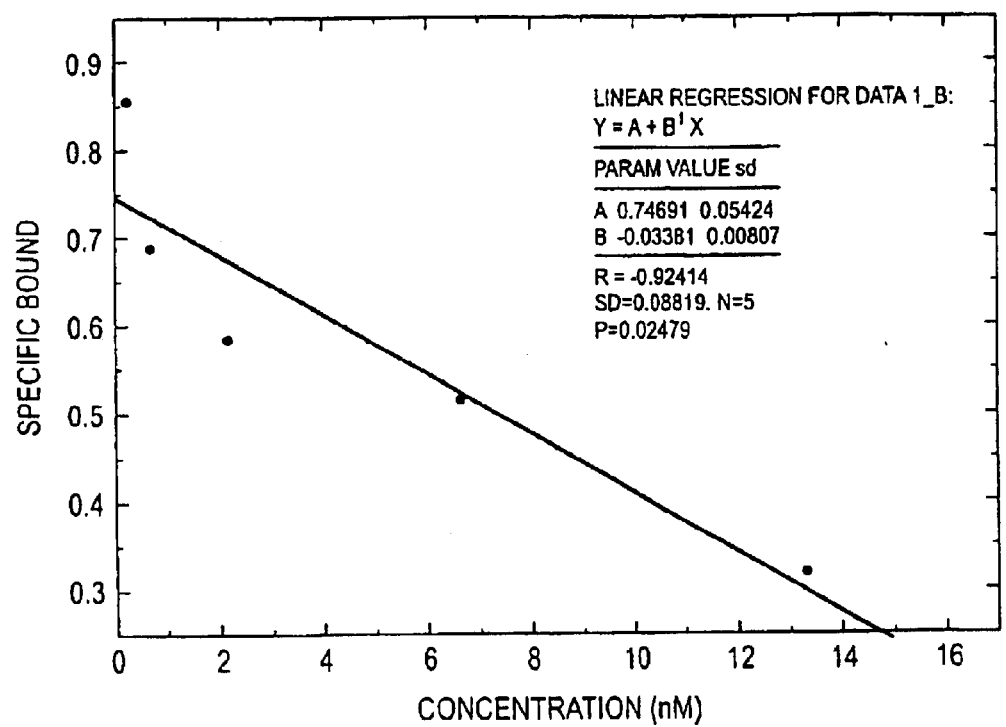

Furthermore, the use of a conjugate according to the present invention to prepare a pharmaceutical solution is disclosed.

10 Claims, 6 Drawing Sheets

RECEPTOR BINDING CONJUGATES

This application claims priority from Norwegian patent application 1999 5978, filed on Dec. 6, 1999.

The present invention relates to a receptor binding conjugate which consists of an antibody, a radionuclide and folate or folate derivative, wherein or not the conjugate possesses dual binding ability. The present invention also relates to a method and a kit to prepare, as well as a method to use such conjugates. Furthermore, the use of a conjugate according to the present invention to prepare a pharmaceutical solution is disclosed.

The use of folate and folate derivatives to target tumours expressing folate binding protein (FBP), a glycosyl-phosphatidyl-inositol-linked cell membrane protein involved in cellular uptake of oxidised folates via endocytosis, has attracted attention among researchers [Kranz et al, 1996; Reddy et al, 1998; Shinoda et al, 1998; Trippet et al, 1999]. As several types of human cancer cells have been shown to overexpress FBP, this receptor may be a possible target for delivery of therapeutic radioisotopes conjugated with folate. It hag been shown that various types of low-molecular weight folate-chelate-radionuclide conjugates could be used to target cells expressing FBP both in vitro and in vivo [Mathias et al, 1998]. However, the pharmacokinetics may not favour small molecules as they generally are rapidly eliminated from the body, and thereby exposing folate receptors in the kidneys to higher concentration of radiopharmaceuticals. Furthermore, the tumour uptake would be limited, as the blood concentration in the target tissues decreases rapidly.

In a previous study, Shinoda et al. (1998) evaluated folate conjugated bovine serum albumin (BSA) labelled with the radionuclide, indium-111, and found that there was a significant difference in pharmacokinetics and biodistribution of non-folate compared to the folate labelled BSA. A high-liver uptake and rapid blood clearance indicated that the folate labelled version of $^{111}$In-BSA was not particularly suitable for radionuclide delivery to tumour cells expressing folate binding protein.

The combination of folate-antibody-radionuclide has to our knowledge not been presented before, although the combination of folate and antibody has been evaluated for other uses Kranz, et al. (1996) conjugated folate to an anti-effector cell antibody with the intent of (1) binding the folate-antibody to folate binding protein on the target cells and (2) affecting lysis of the targeted calls due to the antigen binding portion of the antibody interacted with an effector cell. However, the FBP receptor system has not yet been successfully used to target radionuclides to cancer cells.

In order to target radionuclides to the FBP containing tumours in locoregional settings in particular, it may be advantageous to use larger carriers that do not diffuse too rapidly from the region in which they are injected. Monoclonal antibodies have been raised against the FBP (Campbell et al., 1991), but the problem with monoclonal antibodies is that they usually contains whole protein or peptide sequences from non-human species, and are therefore to a various degree immunogenic when used in humans. This may hamper the use of monoclonal antibodies in protocols requiring repetitive injections because of the appearance of human anti-mouse-antibodies or human anti-chimeric-antibodies, which causes immunocomplexation and unfavourable biodistribution of radioimmunoconjugates (Bruland et al., 1995; Meredith et al., 1993). Also, monoclonal antibodies and their fragments are usually only just monovalent or bivalent (i.e. not multivalent) with respect to antigen combining sites.

It is therefore the object of the present invention to provide an effective receptor selective tumour targeting agent (conjugate) prepared from a carrier molecule (i.e. an antibody), a radionuclide and folate which is chemically linked to the carrier. The conjugate should also simultaneously retain a significant antigen combining ability for the original antigen; i.e. the conjugate possesses dual binding ability. Furthermore, it is an object of the present invention to provide a method to prepare and use such conjugates. These objects have been obtained by the present invention, characterised by the enclosed claims.

The present invention relates to a new class of folate derivatives (conjugates), as well as a method to prepare and use such conjugates. The conjugate consists of (1) an antibody or antibodies preferably of IgG or IgM class. or fragments or constructs (e.g. minibody) thereof, (2) a radionuclide and (3) folate. According to the present invention, the conjugate contains only human proteins/peptides and may have increased avidity, due to the possibility of conjugating multiple folates per antibody, and thereby increasing the probability of binding the conjugate to the target cells. The antibody which is used is either an inert antibody, or a monoclonal antibody with affinity towards a tumour associated antigen. In the first case, a conjugate with FBP affinity alone is constructed, whereas in the second case a conjugate with potentially dual reseptor affinity is made, as the antigen retains a significant antigen combining ability for the original antigen, as well as binding ability for folate to FBP. The principal advantage of dual receptor affinity is that the abundance of target cells without at least one receptor for the conjugate will be reduced, increasing the chances of a succesfull targeting. To our knowledge we are the first to propose the use of folate-antibody-radionuclide to deliver radiation to tumour cells.

The present invention will now be described in more detail, with reference to figures and examples.

Figure 2:
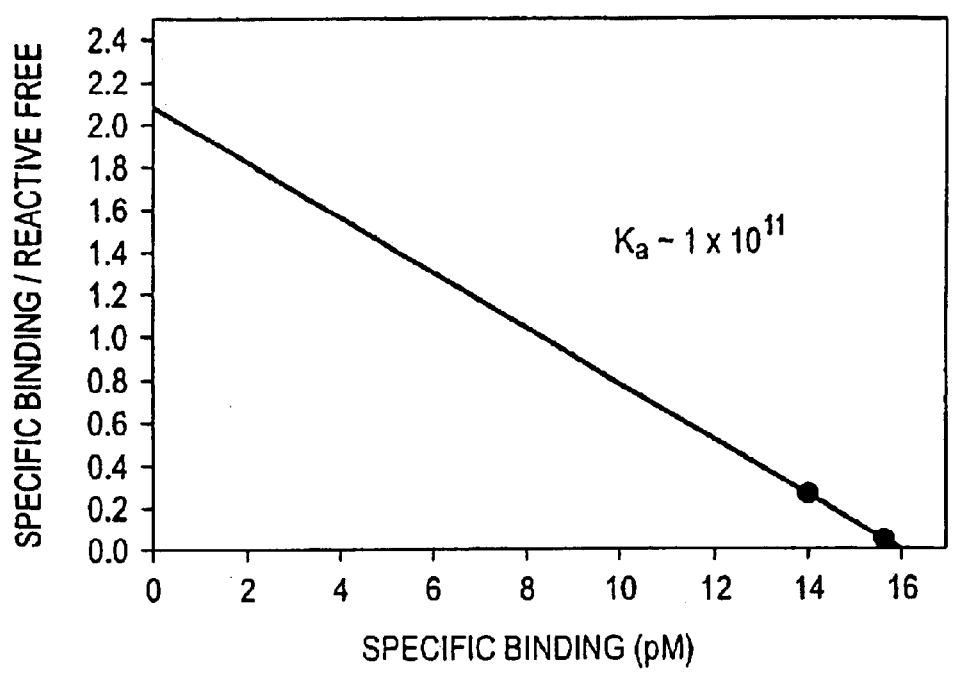
Figure 3:
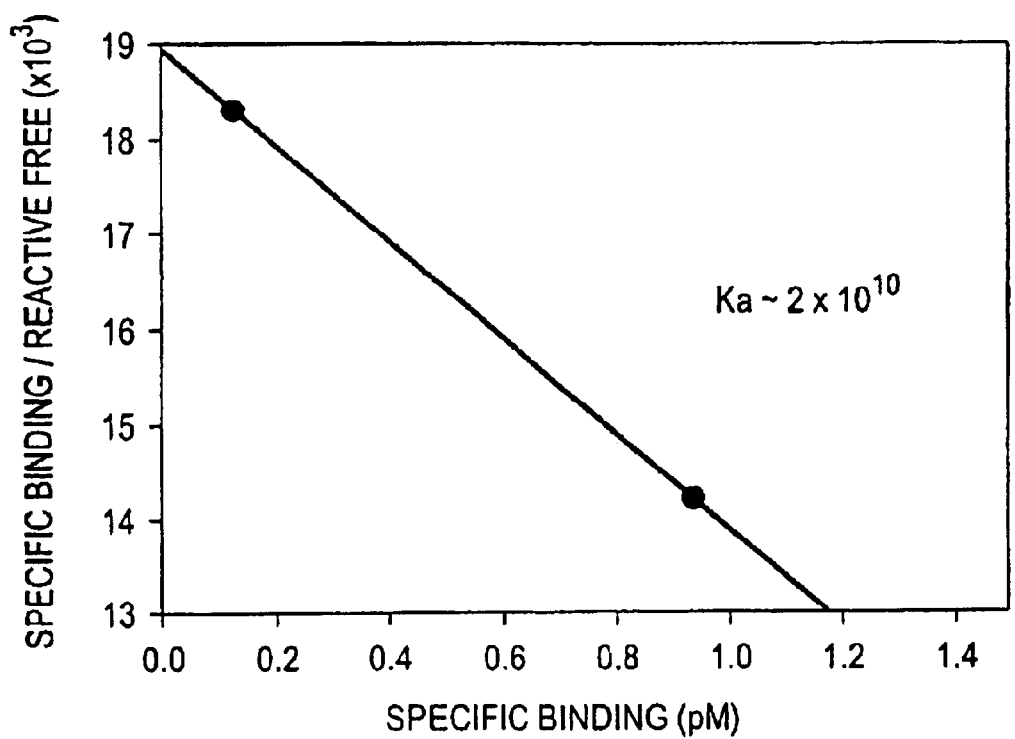
Figure 4:
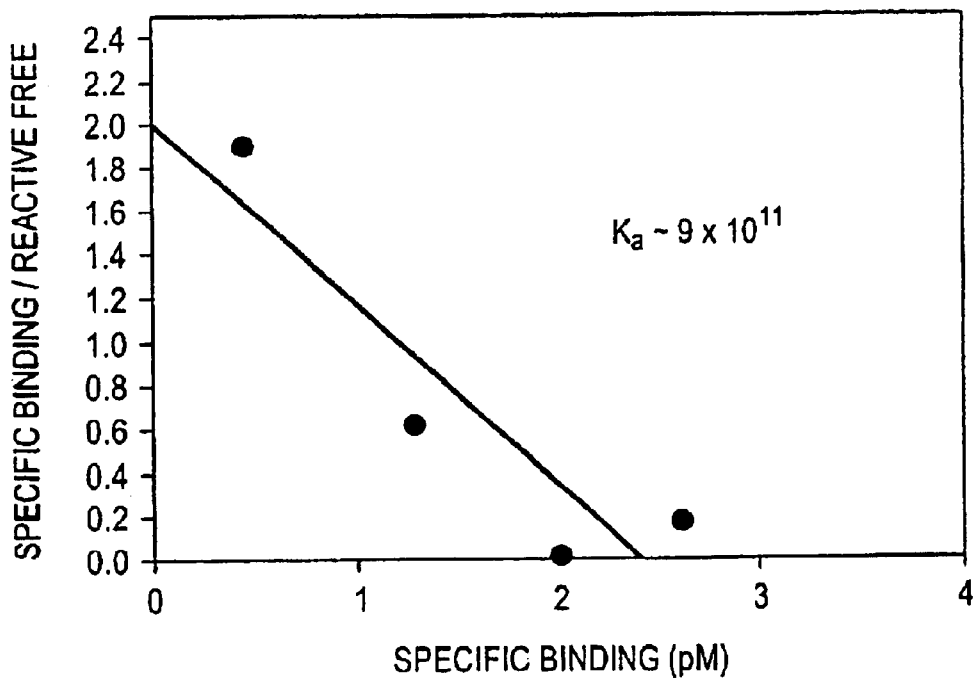
Figure 5:
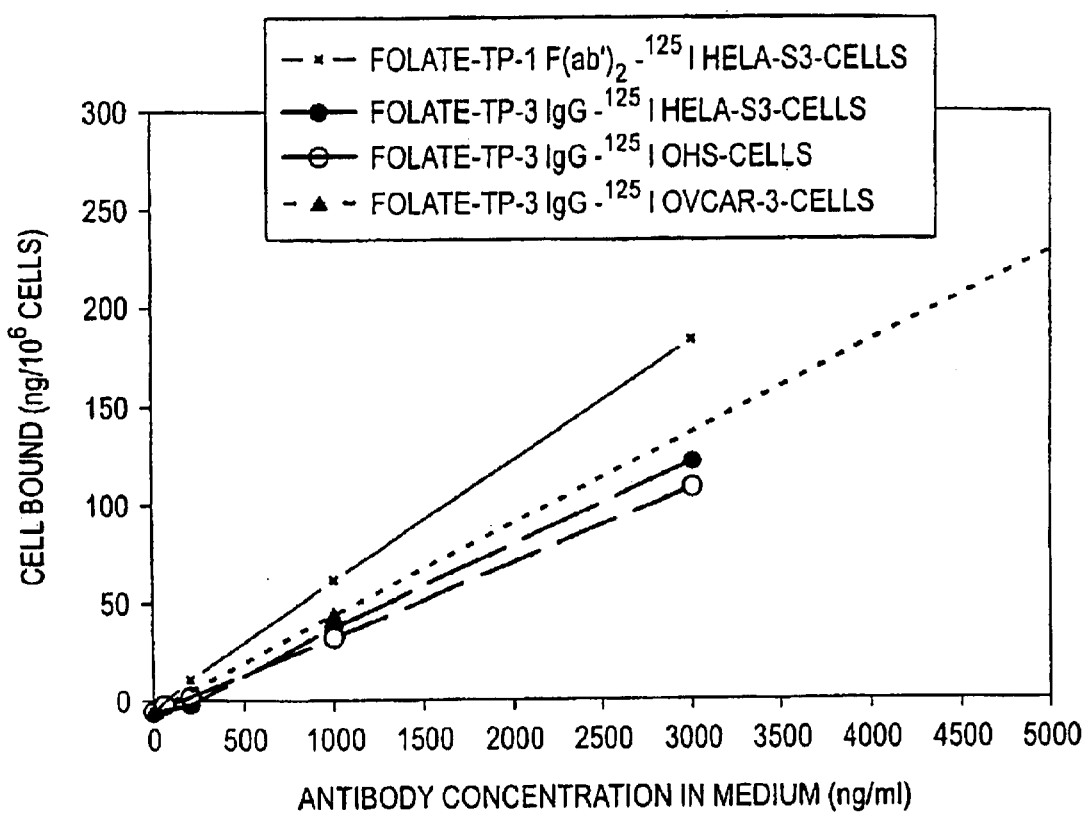
Figure 6:
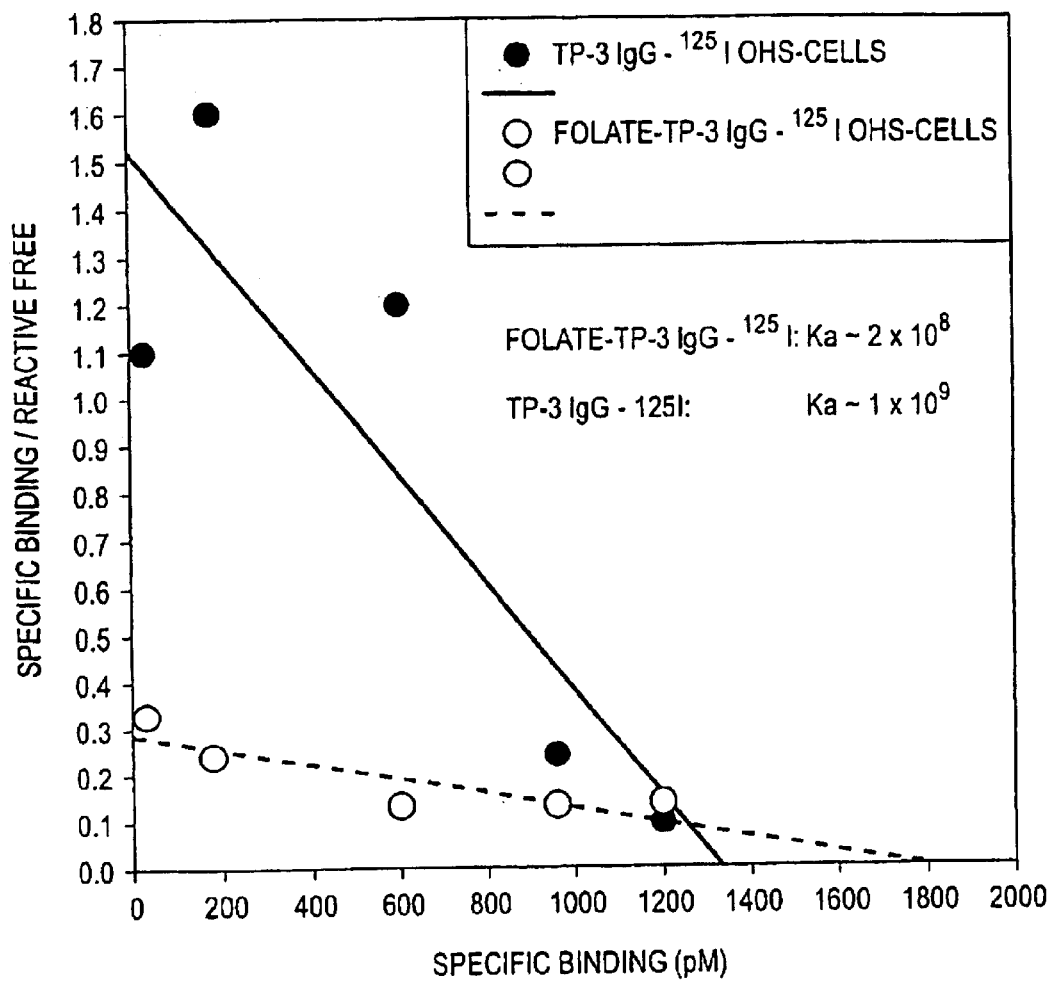

FIG. 1 Binding assay for tritium labelled folate ($^3$H-FA; upper graph) and for folate and iodine-125 labelled polyclonal human IgG ($^{125}$I-FA-HIgG; lower graph), FIG. 2 Folate-TP IgG-$^{125}$I binding to HELA-S3 cells: 10–50 ng/ml range, FIG. 3 Binding assay of Folate-HIgG-$^{125}$I on HELA-S3 cells, 1–10 ng/ml range, FIG. 4 Folate-TP-3 IgG-$^{125}$I binding to OVCAR-3 cells; 0,1–20 ng/ml range, FIG. 5 Specific conjugate binding to cells, FIG. 6 Binding assays of folate labelled Vs non-folated TP-3 IgG monoclonal antibody on OHS cells.

In order to develop a new class of folate derivatives, i.e. to create a new compound (conjugate) that could, if preferred, contain only human protein/peptides, that is multivalent to FBP and that possesses or does not posess dual binding ability, the possibility of using antibodies labelled with folate and radioisotope were elucidated. The advantages of using antibodies in such conjugates are twofold: The larger size of the antibody, compared to small molecular weight compounds, affects the pharmacokinetics of the conjugates, i.e., if injected intravenously it causes a slower blood clearance and sustained concentration of radiopharmaceutical and therefore potential higher tumour uptake; if injected intracavitary it slows down the clearance of radioisotope from the region [Larsen et al. 1995]. Dependent of the degree of folate conjugation (i.e. the avidity, or number of receptor combining units); this conjugate can be multivalent with respect to FBP combining binding sites. Furthermore, by conjugating folate to antibodies having antigen binding ability towards an antigen different from FBP, a conjugate which can bind to two different receptors (i.e. have dual binding ability) is created. For example, if an antibody which is raised against an antigen such as e.g. the anti-osteosarcoma antibody TP-3, is labelled with the folate and radioisotope, it can bind to osteosarcoma cells expressing the antigen by conventional antibody antigen interaction, but also to cells expressing FBP via the folate groups. This dual binding ability principle may be important because the cellular expression of FBP, as well as antigen, may vary in the target cells and subpopulations. Therefore, if the antibody itself also binds to the tumour cells via a different receptor, the probability of achieving a therapeutically sufficient targeting of all of the tumour cells increases. Thus, this principle can be used for targeting two different cell populations each present with only one of the receptors, or it could be used to increase the targeting probability of cells expressing both of the receptors. This type of conjugate can be used in many ways, including for the targeting of therapeutic or diagnostic radioisotopes to cancer cells in vivo.

The dual binding ability principle may also be used for other receptor binding molecules than folate. E.g. oestrogen- and testosterone derivatives could be conjugated to antibodies with affinity for breast or prostate cancer providing a conjugate with dual binding ability for breast cancer or prostate cancer cell.

Additionally we have studied the use of monoclonal antibodies against an osteosarcoma associated antigen in order to show that when radiolabelled and folate labelled, these antibodies could posses dual receptor affinity, i.e., affinity for both the FBP and the osteosarcoma associated antigen.

When we evaluated folate labelled human IgG radiolabelled with astatine-211 and iodine-125 we founds surprisingly, that folate labelled vs. non-folated radiolabelled IgG did not show significant difference in biodistribution in mice. We therefore conclude that folate-antibody-radionuclide conjugate can be useful for in vivo tumour targeting.

The use of the folate-antibody-radioisotope conjugate may be exploited both using intravenous injections as well as for locoregional applications. E.g., conjugates based on short lived radionuclides (i.e. $t_{1/2}$ of a few hours) may be promising for the treatment of intraperitoneally metastasisod ovarian cancer, since this type of cancer has a high probability of overexpressing FBP, and since the clearance of antibodies from the region is relatively slow ensuring a high concentration of radiopharmaceutical in the tumour affected area.

The folate-antibody-carrier molecule can be used to transport different isotopes, e.g., alpha- and/or beta-emitters for therapy, and x-ray and/or gamma emitters and/or positron emitters for tumour scintigraphy and positron-emission-tomography (PET), respectively. Halogen, as described in the experimental section, as well as metal radionuclides, can be conjugated to the folate-antibody, the metal radionuclides by means of bifunctional chelators with coupling reactivity towards, e.g. amino groups (e.g. lysine) in the proteins. Examples of alpha emitters are $^{211}$At, $^{212}$Pb (as a chemical linked generator nuclide), $^{212}$Bi, $^{213}$Bi, $^{222}$Ra, $^{224}$Ra. $^{225}$Ac and $^{227}$Th. Examples of beta-emitters are $^{67}$Cu, $^{90}$Y, $^{131}$I, $^{153}$Sm, $^{166}$Ho and $^{186}$Re. Examples of x-ray emitter and PET nuclide are $^{99m}$Tc and $^{18}$F. A special application would be in radioguided surgery e.g. with $^{125}$I-labelled antibody-folate conjugate.

In general, folate can be coupled to amino groups on ligands by generating an activated ester in the α- or γ-carbonyl position of folate. Several ways of generating activated coupling reagents from folate exist (Readdy et al., 1998). Folate conjugated in the α-position may not show the same receptor activity as the one conjugated in γ-position. It is well known that folate can be coupled to antibodies using the EDC-method (Readdy et al., 1998). This method is not selective for the α- or γ-carbonyl position of folate, but the γ-position is sterically favoured when EDC-method is used. The conjugation of several folates per carrier molecule would ensure that at least one γ-conjugated folate is incorporated (Reddy et al., 1998).

The methods of generating folate-antibody-radionuclide conjugates used herein showed that both amine coupling of radioactive coupling reagent and iodogen labelling of tyrosine could be used to generate a product with folate targeting properties. Probably most general methods for antibody radiolabelling are compatible with folate-labelling. When using amino coupling reagens the radiolabelling yield may be reduced if the antibody is heavily prelabelled with folates due to a reduction in available lysine amines. Radiolabelling can principally be performed before or after folate labelling of the antibody.

The folate-antibody-radionuclide conjugate according to the invention is used to prepare a pharmaceutical solution suitable for injection or infusion into mammals, including humans. This solution is administered to the patient in need thereof via all systemic administration routes known in the art. Examples are intravenous, regional and/or intratumoural routes. Consequently the preparation according to the invention is composed of the active conjugate, optionally adjuvants, pharmaceutically acceptable modifiers, solvents and vehicles, and comprises injection fluids and/or infusion fluids suitable for the selected administration route.

The radioimmunoconjugate according to the invention is further used in combination with other radioimmunoconjugates, folate- and radiolabelled IgG and IgM or fragments thereof and/or other forms of radiopharmaceutical therapy, chemotherapy, external beam therapy or surgery to treat malignancies expressing folate binding protein.

The folate-antibody-radionuclide conjugate is also used in a method to imageing the receptor containing tissues or cells expressing the folate binding protein, or delivering potentially therapeutic radiation to malignant cells expressing the folate binding protein, wherein the malignant tissue is selected from the group comprising e.g. brain, lung, cervix, ovary and breast cancer.

In accordance with the invention it is provided a kit for preparation of the folate labelled antibody or antibody fragment comprising a vial containing a folic acid solution and a vial containing a coupling activating agent (e.g. 1-ethyl-3-(3-diethylaminopropyl)carbodiimide) in solution and optionally a third vial containing a solution with the radioisotope or a ligand, either prelabelled or which can be subsequently labelled with the radioisotope by means of covalent binding or chelation to the antibody or antibody fragment.

The present invention also provides a preparation of a pharmaceutical solution suitable for radiotherapy or radiodetection based on the dual-binding-ability principle where the active component is a conjugate consisting of (1) IgM, IgG or fragments and constructs thereof that is labelled with (2) a radionuclide and (3) in general a molecule (e.g., estrogen or an derivative or testosteron or an derivative) with receptor affinity other than that of the antibody itself.

Best Mode

The receptor binding conjugate according to the invention consists of three components; (1) an antibody or antibodies preferably of IgG or IgM class, or fragments or constructs (e.g. minibody) thereof, (2) a radionuclide or a mixture of radionuclides and (3) folate, wherein or not the conjugate possesses a dual target binding ability, wherein the radionuclide may be selected from $^{211}$At or $^{125}$I.

The method to prepare a receptor binding conjugate consisting of three components, (1) an antibody or antibodies preferably of IgG or IgM class, or fragments or constructs (e.g. minibody) thereof, (2) a radionuclide or a mixture of radionuclides and (3) folate, comprises using standard procedures for radionuclide labelling and folate labelling of the antibody.

Generally the preparation conditions must be optimized for each antibody labelled because of differences in the number of, and localization of (e.g. antibody combining sites or the non binding region) lysine units.

Pretreatment of the IgG

The bath of antibody is subject to buffer exchange using a Sephadex PD-10 column (Pharmacia) pre-equilibrated with the buffer used for giving the optimal folate labelling conditions for that particular antibody, (e.g., 0.05 M borate at pH 8.5). The antibody is eluted through the column and, if required, diluted with buffer to obtain a concentration suitable for performing the labelling steps (e.g., 1–50 mg/ml).

The process which is described, in detail in the enclosed examples, meant to be clairifying but not limiting, consists of the following steps:

Folate Labelling

The general procedure is described in the experimental section. Firstly, folate is conjugated to the antibody (typically 1–20 folate per antibody). Coupling activated folate in solution is added to antibody and the and the reaction is left to proceed for less than 10 s to more than 2 days. The reaction may be quenched e.g., by adding excess of glysine in borate buffer. The resulting conjugate is purified using gel filtration separation (size exclusion e.g., Sephadex G-25 PD-10 column). Secondly, the folate labelled antibody is radiolabelled with a radionuclide. The final product is purified by gel filtration using, e.g., a Sephadex G-25 PD-10 column.

Radiolabelling may be performed subsequent to folate conjugation. Standard radiolabelling procedures, as described in detail in the experimental section, can be used. Radiolabelled conjugates can be prepared with specific activity ranging from less than 1 Bq/mg to several GBq/mg of antibody.

EXAMPLES

Example 1

Conjugation of Folate to Human IgG

Pre-Treatment of the IgG

Commercially available human IgG (HIgG) (Gammanorm; Pharmacia & Upjohn) at an initial concentration of 165 mg/ml in buffer of glycine, NaCl and NaAc was used.

H-IgG was separated from small molecular weight components by eluting the mixture on a Sephadex G-25 column, (PD-10, Pharmacia) preequillibrated with PBS.

The IgG concentration was determined by absorbance readings at=280 nm using an extinction coefficient for the protein of 224 000.

The elution profile of purified HIgG on size exclusion HPLC using TSK-G3000 SW$_{xi}$ column (Toso Haas) showed essentially one peak corresponding to the IgG.

(HPLC system; Shimadzu, LC-10AT pump, SPD-M10A Diode array detector).

Conjugation of Folic Acid

To ensure reactivity, a stock solution of folic acid was prepared by dissolving commercially available folic acid (Sigma) in dimethyl sulfoxide with a H$_2$O content less than 0.05%. The solution was then cannulated into a bottle containing activated 4 Å sieves (Fluka) and stored under an argon atmosphere in the dark for 6–10 hours.

$^3$H-Folic acid (Amersham Pharmacia Biotech, Buckinghamshire, England) was included as a tracer in the folic acid preparation and was added as an aqueous solution of the potassium salt of $^3$H-Folic acid (1% with respect to citric acid) and thereafter desiccated at 8 mTorr for 3 days. The folic acid containing $^3$H-Folic acid was thereafter treated as described above. The folic acid was activated for coupling to the HIgG, by adding 4–10 mol equivalents of 1-ethyl-3-(3-dimethylaminopropyl) carbondaiimide to the folic acid solution and incubating for 30 min at ambient temperature. Thereafter, a 20–60-fold molar excess of the activated folic acid was added to H-IgG (15 mg/ml) in PBS and allowed to react for 30–60 min. The reaction was quenched by adding 0.2 ml of 0.3 M glycine in PBS/borate, pH 8.5. The folic-acid HIgG conjugate (FA-HIgG) was separated from unreacted material using a PD-10 column preequillibrated in PBS. Individual fractions was assayed for the presence of HIgG aggregates/dimers/fragments or low molecule or weight components by size exclusion HPLC.

The extent of folic acid conjugation was determined by the $^3$H-content of the purified FA-HIgG as measured by liquid scintillation counting (Beckmann LS 6500) combined with the determination of the protein concentration spectrophotometrically; the protein concentration was determined by the absorption at 280 nm correcting for the contribution to the absorption that is due to folic acid at this wavelength as calculated from the extinction coefficient and the concentration of folic acid obtained from the $^3$H measurements.

Example 2

Preparation of $^{125}$I-FA-HIgG and $^{211}$At-FA-HIgG

Radioiodination by the Iodogen Method

FA-HIgG in PBS (typically 2–5 mg/ml) was iodinated by the Iodogen method using standard methodology (Fraker et al., 1978) The radiolabelled product was purified by PD-10 and assayed on HPLC size exclusion column. This study indicated that the yield of radiolabelled product was similar if the antibody was labelled with folate before or after radiolabelling.

Radiolabelling Using the N-succinimidyl-3-[$^{125}$I] iodobenzoate (ATE-Method)

Folate-labelled antibody or antibody alone, at typically concentrations 1–10 mg/ml in borate buffer (pH 8–9), were added to a dry vial containing either N-succinimidyl-4-[$^{211}$At]astatobenzoate or N-succinimidyl-3-[$^{125}$I] iodobenzoate. The two labelling reagents had been prepared as described (Larsen et al., 1994b). After 15 min. of gentle agitation of the vial 0.3 ml 0.2 M glycine in borate (pH 8–9) was added and the vial agitated for additional 5 min. Thereafter the solution was transferred to a Sephadex G-25 PD10 column (Pharmacia) and the radiolabelled IgG was eluted using a PBS buffer (pH 7.4).

Results: The overall labelling yield were in the range of 35–60% using this method. These procedures were used for TP-3, Rituximab and human polyclonal IgG as well as TP-1 F(ab')$_2$ and could be performed in similar fashion with N-succinimidyl-[$^{211}$At]astatobenzoate (Larsen et al., 1994)

In an experiment to determine protein bound fraction of $^{211}$At and $^{125}$I the purified product were evaluated using methanol precipitation of the protein. More than 97% of the radioactivity precipitated for the $^{125}$I-FA-HIgG, $^{211}$At-FA-HIgG, $^{125}$I-HIgG and $^{211}$At-HIgG preparations.

Example 3

Biodistribution of $^{125}$I-FA-HIgG and $^{211}$At-FA-HIgG Versus $^{125}$I-HIgG and $^{211}$At-HIgG Methods: A single FA-HIgG preparation with an average FA/HIgG ratio of 2,3 was used for the preparation of both $^{125}$I-FA-HIgG and $^{211}$At-FA-HIgG and for comparison $^{125}$I-HIgG and $^{211}$At-HIgG were also prepared as described in example 2.

White female Balb/C mice with a body weight in the range of 16–20 g were used in the biodistribution experiment. The compounds were administered by intraperitoneal injection of 500 µl of the preparation to each animal. The compounds were administered in paired label arrangement ($^{211}$At-FA-HIgG vs. $^{125}$I-HIgG and $^{125}$I-FA-HIgG vs. $^{211}$At-HIgG) using approximately 100 kBq of $^{211}$At and 50 kBq of $^{125}$I for each animal. Animals were sacrificed by cervical dislocation and the tissue distribution determined at 1, 6 and 24 hours using groups of 3 mice at each time point and performing the experiments in two series, reversing the label vs. antibody type (with respect to folate). The radioactivity contents of the tissue samples were measured on a NaI (Tl) well-type detector. Firstly, the window and threshold of the detector were adjusted in order to measure $^{211}$At disintegrations with no detectable crossover from $^{125}$I. Secondly, after a time period corresponding to 20 half-lives of $^{211}$At, the tissue samples were measured again for quantification of the $^{125}$I content. Samples of radiolabelled HIgG preparations with a single nuclide and mixtures of the nuclides were used as references.

Results: Table 1 shows the distribution ratio between folate labelled and non-folated radiolabelled HIgG. The ratios were kept between 0.7–1.9 at all points indicating only minor distribution changes in a few tissues as the effects of the folate label on the antibody. No significant effect of the folate label was determined for the kidneys which is considered a sensitive tissue because of folate binding receptors. In general, the folate labelling had no major impact of the biodistribution of radiolabelled antibody indicating folate labelled radioimmunoconjugates may be useful for in vivo applications.

Conclusion: Renal clearance of the folate labelled IgG appeared to be slow preventing accumulation at folate binding receptors in the kidneys. Folate labelling also had no major impact on the biodistribution of radiolabelled HIgG in other tissues, indicating that folate- and radiolabelled IgG could be useful tools for cancer treatment.

TABLE 1

Ratio of distribution[1] of folate labeled vs non folated radiolabeled human IgG performed in "paired label" fashion using astatine-211 and iodine-125.

| Tissue | 1 h | 6 h | 24 h |
| --- | --- | --- | --- |
| Blood | 1.2 ± 0.3 | 1.2 ± 0.5 | 0.7 ± 0.3 |
| Kidney | 1.2 ± 0.7 | 0.9 ± 0.3 | 0.9 ± 0.2 |
| Liver | 1.5 ± 0.2 | 1.5 ± 0.6 | 0.8 ± 0.3 |
| I. P. Fat | 1.2 ± 0.1 | 1.1 ± 0.4 | 1.1 ± 0.3 |
| Neck | 1.9 ± 1.2 | 1.0 ± 0.6 | 1.5 ± 0.8 |
| Lung | 1.2 ± 0.3 | 1.0 ± 0.1 | 0.8 ± 0.1 |
| Muscle | 1.3 ± 0.1 | 0.9 ± 0.1 | 0.8 ± 0.1 |
| Heart | 1.3 ± 0.4 | 1.0 ± 0.1 | 0.8 ± 0.3 |
| Sm. Intestine | 1.3 ± 0.4 | 1.2 ± 0.2 | 0.9 ± 0.1 |

TABLE 1-continued

Ratio of distribution[1] of folate labeled vs non folated radiolabeled human IgG performed in "paired label" fashion using astatine-211 and iodine-125.

| Tissue | 1 h | 6 h | 24 h |
| --- | --- | --- | --- |
| L. Intestine | 1.9 ± 0.2 | 1.6 ± 0.2 | 1.0 ± 0.1 |
| Spleen | 1.5 ± 0.1 | 1.3 ± 0.3 | 1.0 ± 0.2 |
| Stomach | 1.3 ± 0.1 | 1.3 ± 0.9 | 1.4 ± 1.3 |
| Femur | 1.7 ± 0.6 | 1.0 ± 0.1 | 0.7 ± 0.1 |

[1]The experiment were performed in two series, 3 animals per time points in one serie. Combination of radiolabel and antibody type (folate labeled vs non-folated) was reversed between the two series.

Example 4

Binding Assay of Folic Acid and Folic Acid Conjugates

Immobilised folate binding protein (FBP) was used to investigate the binding characteristics of the folic acid conjugates. FBP (Sigma) with a binding capacity of 2.5 g folic acid per milligram protein was immobilised on high protein binding 96 well EIA/RIA assay plates (Costar Corning Inc. N.Y., USA)

Investigation of the Immobilisation of Folate Binding Protein

FBP was labelled with $^{125}$I by the Iodogen method and the labelled protein was isolated by eluting the reaction mixture on a PD-10 column. Purified $^{125}$I-FBP in concentrations ranging form 5–20 g/ml in PBS were added in to the 96 well assay plates and incubated on a rotating rack at 4° C. overnight. The liquid in the wells were removed (L1) and the wells were thereafter washed four times with PBS (L2) (room temp.). After this, the wells were added 2M NaOH and were allowed to stand approximately 1 h at room temperature before the liquid was removed (L3). The immobilised quantities of the various concentrations of quadruplicates of $^{125}$I FBP was determined as the ratio of L3/L1+ L2 after measuring the radioactivity of the respective samples by liquid scintillation counting. Conditions that resulted in an average of 1 g FBP immobilised on the wells were used in the binding assays of $^3$H-FA and $^{125}$I-FA-HIgG.

Binding of $^3$H-FA to Immobilised Folate Binding Protein

Wells were incubated with a solution of FBP in PBS and washed three times with PBS after removal of the incubation mixture. One half of the number of coated wells were added a 5 M solution of folic acid in PBS, the other half were added PBS only. After 1 h at room temperature, the liquid was removed and thereafter folic acid in concentrations ranging from 0,1 to 2.8 nM (6 parallels) containing $^3$H-FA was added to the wells and incubated at 4° C. overnight. The specifically bound fraction of folic acid was determined by a similar method as described for $^{125}$I-FBP, correcting for the faction of $^3$H-FA retained in the wells that were preincubated with folic acid.

Binding of $^{125}$I-FA-HIgG to Immobilised Folate Binding Protein

Wells were incubated with a solution of FBP in PBS and washed two times with PBS after removal of the incubation mixture and subsequently with a solution of HIgG in PBS (10 g/ml). Half of the number of coated wells were added a 5 M solution of folic acid in PBS, the other half were added PBS only. After 1 h at room temperature, the liquid was removed and the wells were added $^{125}$I-FA-HIgG in concentrations ranging from 0.2(4) to 13,(3) nM with respect to the conjugated folic acid (5 parallels). The specifically bound $^{125}$I-FA-HIgG was determined as described above for $^3$H-FA.

Determination of Binding Properties

The specifically bound $^3$H-FA was plotted against the concentration of $^3$H-FA in a Scatchard type plot (FIG. 1). For $^{125}$I-FA-HIgG, a similar plot was made assuming the presence of at least one binding-reactive folic acid derivative on each HIgG molecule. The following values were determined from the binding assay:

$K_a$ was determined from the plot with $^3$H-FA: $2\times10^8$ $K_a$ was determined from the plot with $^{125}$I-FA HIgG: $0.5\times10^5$ (It should be noted that a two component plot could also be a possible solution to the points since if only the three lowest concentration points are considered a significant higher $K_a$-value would be obtained).

Conclusion: The radiolabelled folate-IgG conjugate showed a significant binding affinity towards the receptor (folate binding protein).

Example 5

Antigen Binding Ability of Folate- and Radioisotope Labelled TP-3 IgG and TP-1 F(ab')$_2$ on OHS-Cells.

The TP-3 and TP-1 monoclonal antibodies (Bruland et al., 1986) binds to two different epitopes of an cell-surface antigen expressed on osteosarcoma cells (Bruland et al., 1988)., These antibodies were used to study the effect of folate conjugation on the antibodies ability to bind to the antigen in vitro. OHS cells were grown according to standard methods (Larsen et al. 1994a) but using 10% fetal calf serum in stead of 13%. Cells were harvested added DMSO and frozen at −80° C.

Methods: TP-1 F(ab')2 and TP-3 IgG were folate labelled, (as described above) to obtain folate:antibody ratios of 2:1 and 4.1 respectively. Folate-labelled as well as non-folated versions of the TP-3 and TP-1F(ab')$_2$ were subsequently radiolabelled using N-succinimidyl-3-[$^{125}$I]Iodobenzoate as described in example 1. Frozen batches of OHS osteosarcoma cells which on average expressed $7.4\times10^5$ antigens per cell (Larsen et al., 1994a) were melted washed and centrifuged twice with PBS to remove DMSO and suspended in PBS (containing 1% BSA) to a concentration of 4 million cells per ml. To 4 ml test tubes were added 0.3 ml of this suspension. Thereafter 0.5 ng of one of the four conjugates $^{125}$I-TP1 (Fab')$_2$-folate; $^{125}$I-TP-1 F(ab')$_2$; $^{125}$I-TP-3 IgG-folate; was added to the tubes. Sample tubes were subsequently incubated for three hours, whereafter the tubes were counted for radioactivity on a NaI counter, washed and centrifuged three times before cell pellet associated radioactivity was counted. The Retained cell binding ability (RCBA) was determined as follows:

RCBA=cell binding fraction of folate labelled RIC/cell binding fraction of non-folated RIC RIC; radioimmunoconjugate Results: The RCBA of $^{125}$I-TP-3 IgG-folate vs $^{125}$I-TP-3 IgG was 0.36 while the RCBA for $^{125}$I-TP-1 F(ab')$_2$-folate vs. $^{125}$I-TP-1 F(ab')$_2$ was 0.62. This indicates that although some immunoreactivity was lost, antibodies were still reactive with the osteosarcoma associated antigen.

Conclusion: Antibodies labelled with folate can in principle react with both the antigen and folate binding protein, i.e., such conjugate possesses dual binding ability Example 6

Binding of Folate- and Radio-Labelled Antibodies to OVCAR-3 and HELA-S3 Cells Expressing Relate Binding Protein. Demonstrating Dual Binding Ability Using OHS Cells.

Methods: OVCAR-3 cells (human ovarian carcinoma), HELA-S3 (human cervical carcinoma) were used as folate expressing cells. The cells were cultured in 75 cm$^2$ plastic flasks supplemented with RPMI 1640 Medium supplemented with 10% fetal calf serum, penicillin, streptomycin and glutamine. 10 days prior to harvesting the culture medium was replaced with folate-free RPMI 1640 medium supplemented with 10% calf serum to ensure the expression of folate binding protein before the cells were harvested. Harvested cells were added DMSO and frozen at −80° C. Prior to use in the binding assays the frozen cells were melted and immediately added PBS containing 1% BSA and washed and centrifuged twice to remove the DMSO. Suspension of cells in PBS with 1% BSA were kept on ice during incubation with conjugates. Binding assays were performed as follows: Stock cell suspensions of OVCAR-3 and HELA-S3 of 1 million cells per ml were made and 0.5 ml were added to 2 ml test tubes. The tubes were added various amounts of folate-antibody-$^{125}$I. To determine non-specific binding parallel tubes were added non-folated antibody-$^{125}$I at the same concentrations. The tubes were incubated on a shaker for 3 hours counted for radioactivity and washed. Finally the cell pellet associated radioactivity was counted. The following conjugates were evaluated: folate-TP-1 F(ab')$_2$-$^{125}$I (~2 folate per antibody molecule, labelled with SIB (SIB=N-succinimidyl-3-[$^{125}$I] iodobenzoate), 50 MBq/mg); TP-1 F(ab')$_2$-$^{125}$I (SIB-labelled, 90 MBq/mg); folate-TP-3-IgG-$^{125}$I (~4 folate per antibody molecule, SIB-labelled, 70 MBq/mg); TP-3-IgG-$^{125}$I (SIB-labelled, 120 MBq/mg) folate-HIgG-$^{125}$I (iodogen-labelled, 400 MBq/mg).

An additional experiment was performed by incubating folate-TP-3-IgG-$^{125}$I and TP-3-IgG-$^{125}$I with OHS cells and using the data for TP-3-IgG-$^{125}$I incubated with HELA-S3 as non-specific control.

Results: preliminary data indicates that there are at least two types of interaction with folate binding protein, One which has a high affinity and saturates at low concentration (typically below 50 ng/ml). $K_a$' in the range of $10^{10}$–$10^{12}$ was determined with the limited data points available at these low concentrations (FIGS. 2–4). In a one point assay, using 0.1 ng/ml concentration of folate-TP-3-IgG-1$^{125}$I (and 0.1 ng TP-3-IgG-$^{125}$I as control of non-specific binding) and $5\times10^5$ OVCAR-3 cells in 0.5 ml, it was found that 67% of the folate-antibody-radionuclide bound specifically to the cells. At higher concentrations binding of lower affinity appeared to occur (FIG. 5). Saturation of the binding did not seem to occur even for conjugate concentrations in $\mu$g/ml range. The cell-binding appeared to be increasing linearly with increases in the medium concentration of folate-antibody-radionuclide conjugates. It should be noted that the specific uptake for folate-TP-3-IgG-$^{125}$I on OHS was similar to that on the HELA-S3 and OVCAR-3 when corrected for non-specific binding (FIG. 5). The affinity of folate-TP-3-IgG-$^{125}$I (4 folates per antibody) was compared to that of non-folated TP-3-IgG-$^{125}$I (FIG. 6). Both TP-3 versions had a significant affinity towards OHS cells. The data indicates a reduction in $K_n$ of about five for the folated version compared to the non-folated version of the TP-3 IgG antibody, probably due to modification of lysine in the antigen combining sites.

Conclusion: Folate-antibody-radionuclide conjugates show a significant binding to folate binding protein (FBP) on cells indicating that these conjugates may be used to target FBP-expressing tumour cells in vivo. Also, as demonstrated by specific binding of folate-TP-3-IgG-$^{125}$I to antigen-positive OHS cells as well as FBP-positive HELA-S3 and OVCAR-3 cells, folate-antibody-radionuclide conjugates can possess dual binding ability.

LITERATURE

Bruland, Ø, Fodstad, Ø, Stenwig, A E and Pihl, A. Expression and characteristics of a novel human osteosarcoma-associated cell surface antigen. *Cancer Res* 48, 5302–5309 (1988).

Bruland, Ø, Fodstad, Ø, Funderud, S and Pihl, A. New monoclonal antibodies specific for human sarcomas. *Int J Cancer* 38: 27–31 (1986).

Bruland, ØS. Cancer therapy with radiolabelled antibodies. An overview. *Acta Oncol* 34, (8) 1085–1094, (1995).

Campbell, I G, Jones, T A, Foulkes, W D, Trowsdale J. Folate-binding protein is a marker for ovarian cancer. *Cancer Res* 51, 5329–5338 (1991).

Fraker, P J and Speck Jr. J C Protein and cell membrane iodination with a sparingly soluble chloramine, 1, 3, 4, 6-tetrachloro-3a, 6a-diphenyl glucoluril. *Biochem Biophys Res Comm* 80, 849–855 (1978).

Kranz, D M, Roy, E J and Patrick, T A, Conjugates of folate anti-effector cell antibodies, U.S. Pat. No. 5,547,668 (Aug. 20, 1996).

Larsen, R H, Bruland, ØS, Hoff, P, Alstad, J, Lindmo, T and Rofstad, E K. Inactivation of human osteosarcoma cells in vitro by $^{211}$At-TP-3 monoclonal antibody: Comparison with astatine-211-labelled bovine serum albumine, free astatine-211 and external beam X rays. *Radiat Res* 139, 178–184 (1994a).

Larsen, R H, Hoff, P, Alstad, J and Bruland, ØS. Preparation and quality control of $^{211}$At-labelled and $^{125}$I-labelled monoclonal antibodies. Biodistribution in mice carying human osteosarcoma xenografts. *J Labelled Compds Radiopharmaceuticals.* 34 (8): 773–785 (1994b).

Larsen, R H, Hoff P. Vergote, I B, Bruland, ØS, Aas, M, De Vos, L and Nustad, K. α-particle radiotherapy with $^{211}$At-labelled monodisperse polymer particles, $^{211}$At-labelled IgG proteins, and free $^{211}$At in a murine intraperitoneal tumour model *Gynecol Oncol.* 57: 9–15 (1995).

Mathias, C J, Wang, S., Waters, D J, Turek, J J, Low, P S and Green, M A. Indium-111-DTPA-Folate as a potential folate receptor targeted radiopharmaceutical. *J Nucl Med* 39: 1579–1585 (1998).

Meredith, R F, Khazaeli, M B, Plott, W E, LIU, T., Russel, C D, Wheeler, R H and Lobuglio, A F. Effect on human immune-response on repeat courses of I-131 chimeric B72.3 antibody therapy. *Antibody, Immunoconj Radiopharm* 6 (1), 39–46 (1993).

Reddy, J A and Low, P S Folate-mediated targeting of therapeutic and imaging agents to cancers. *Critical Reviews in Therapeutic Drug Carrier Systems* 15 (6): 587–627 (1998).

Shinoda, T, Takagi, A, Macda, A, Kagatani, S, Konno, Y and Hashida, M. In vivo fate of folate-BSA in non-tumour- and tumour-bearing mice. *J Pharm Sci* 87 (12): 1521–1526, 1998.

Trippett, T M and Bertino, J R. Therapeutic strategies targeting proteins that regulate folate and reduced folate transport. *J Chemotherapy* 11: 3–10 (1999).

What is claimed is:

1. A method of delivering therapeutic radiation to a patient with a malignant cell expressing a folate binding protein comprising administering to said patient a conjugate consisting essentially of (1) an inert human IgG or IgM antibody or antibodies or a fragment or construct thereof, (2) a radionuclide or a mixture of radionuclides, and (3) a folate that binds to said folate binding protein, and wherein said malignant cell is derived from brain, lung, cervical, ovarian, or breast tissue.

2. The method of claim 1, wherein said radionuclide is selected from the group consisting of an alpha emitter, a beta emitter, a gamma emitter, a positron emitter, and an x-ray emitter.

3. The method of claim 2, wherein said alpha emitter is $^{211}$At, $^{212}$Bi, $^{213}$Bi, $^{212}$Pb, $^{225}$Ac, $^{223}$Ra, $^{224}$Ra or $^{227}$Th.

4. The method of claim 2, wherein said beta emitter is $^{131}$I, $^{90}$Y, or $^{153}$Sm.

5. The method of claim 1, wherein said radionuclide is $^{211}$At or $^{125}$I.

6. The method of claim 1, wherein said conjugate is administered intravenously, regionally, or intratumorally.

7. The method of claim 1, wherein said method further comprises treating said patient with an additional form of radiopharmaceutical therapy, with chemotherapy, with external beam therapy, or with surgery.

8. The method of claim 1, wherein said conjugate is administered at a concentration of 0.1–20 ng/ml.

9. The method of claim 1, wherein said conjugate is administered at a concentration of 1–10 ng/ml.

10. The method of claim 1, wherein said conjugate is administered at a concentration of 10–50 ng/ml.

* * * * *

UNITED STATES PATENT AND TRADEMARK OFFICE
CERTIFICATE OF CORRECTION

PATENT NO. : 6,740,304 B1
DATED : May 25, 2004
INVENTOR(S) : Roy H. Larsen and Gjermund Henriksen It is certified that error appears in the above-identified patent and that said Letters Patent is hereby corrected as shown below:

Column 1,
Line 43, replace "uses" with -- uses. --; and
Line 46, replace "calls" with -- cells --.

Column 2,
Line 15, replace "class." with -- class --;
Line 26, replace "reseptor" with -- receptor --;
Line 32, replace "successfull" with -- successful --; and
Line 52, replace "posess" with -- possess --.

Column 3,
Line 23, replace "oestrogen-" with -- oestrogen --;
Line 44, replace "metastasisod" with -- metastasised --; and
Line 61, replace "$^{224}$Ra." with -- $^{224}$Ra, --.

Column 4,
Lines 2 and 6, replace "Readdy" with -- Reddy --;
Line 17, replace "reagens" with -- reagents, --;
Line 40, replace "imageing" with -- image --;
Line 63, replace "estrogen or an" with -- estrogen or a --; and
Line 63, replace "testosteron or an" with -- testosterone or a --.

Column 5,
Line 7, replace "components," with -- components; --; and
Line 33, replace "and the and the" with -- and the --.

Column 6,
Line 16, replace "carbondaiimide" with -- carbodiimide --.

Column 7,
Line 9, replace "2,3" with -- 2:3 --.

Column 8,
Line 30, replace "form" with -- from --; and
Line 53, replace "faction" with -- fraction --.

UNITED STATES PATENT AND TRADEMARK OFFICE
CERTIFICATE OF CORRECTION

PATENT NO. : 6,740,304 B1
DATED : May 25, 2004
INVENTOR(S) : Roy H. Larsen and Gjermund Henriksen It is certified that error appears in the above-identified patent and that said Letters Patent is hereby corrected as shown below:

Column 9,
Line 24, replace "1988).," with -- 1988). --;
Line 28, replace "in stead" with -- instead --;
Line 32, replace "4.1" with -- 4:1 --;
Line 37, replace "melted" with -- melted, --; and
Line 59, replace "ability" with -- ability. --.

Column 10,
Line 35, replace "One" with -- one --.

Column 12,
Delete Claims 8, 9 and 10.

Signed and Sealed this

Fifteenth Day of November, 2005

JON W. DUDAS
*Director of the United States Patent and Trademark Office*